(12) United States Patent  
Rutynowski

(10) Patent No.: US 7,842,059 B2
(45) Date of Patent: Nov. 30, 2010

(54) PUNCTURING DEVICE

(75) Inventor: Wlodzimierz Rutynowski, Warsaw (PL)

(73) Assignee: "HTL Strefa" Spolka Akcyjna, Ozorkow (PL)

( * ) Notice: Subject to any disclaimer, the term of this patent is extended or adjusted under 35 U.S.C. 154(b) by 320 days.

(21) Appl. No.: 10/565,395

(22) PCT Filed: Dec. 1, 2003

(86) PCT No.: PCT/PL03/00132

§ 371 (c)(1), (2), (4) Date: Jul. 5, 2006

(87) PCT Pub. No.: WO2005/009238

PCT Pub. Date: Feb. 3, 2005

(65) Prior Publication Data

US 2007/0135828 A1 Jun. 14, 2007

(30) Foreign Application Priority Data

Jul. 29, 2003 (PL) .................................. 361490

(51) Int. Cl.
A61B 17/32 (2006.01)
(52) U.S. Cl. ........................ 606/181; 606/182
(58) Field of Classification Search .................. 606/181, 606/182, 183; 600/573, 583; 604/110, 192, 604/194, 195
See application file for complete search history.

(56) References Cited

U.S. PATENT DOCUMENTS

| 4,527,561 | A | * | 7/1985 | Burns ........................ 606/182 |
| 5,356,420 | A | * | 10/1994 | Czernecki et al. ........... 606/182 |
| 5,628,765 | A | * | 5/1997 | Morita ...................... 606/182 |
| 5,755,733 | A | * | 5/1998 | Morita ...................... 606/182 |
| 6,053,930 | A |   | 4/2000 | Ruppert ..................... 606/181 |
| 6,358,265 | B1 | * | 3/2002 | Thorne et al. ............... 606/181 |
| 2005/0222599 | A1 | * | 10/2005 | Czernecki et al. ........... 606/182 |
| 2008/0103517 | A1 | * | 5/2008 | Takemoto et al. ........... 606/182 |

OTHER PUBLICATIONS

International Search Report.

* cited by examiner

Primary Examiner—Anhtuan T Nguyen
Assistant Examiner—Jonathan W Miles
(74) Attorney, Agent, or Firm—Plumsea Law Group, LLC

(57) ABSTRACT

The device is built of a housing (1), wherein a push button (3) is positioned, and the puncturing needle (5), wherein the push button (3) has arms (7, 8) to guide the push button (3) inside the housing (1), and a driving spring (11), one end of which is linked to the push button (3), and the other end drives the puncturing needle (5), and the puncturing needle (5) has breakable wings (17, 18), which rest against the breaking edge (19) of the housing (1). The device has moreover two return springs (13, 14), each of which is connected to one of the arms (7, 8) of the push button (3), and two side juts (15, 16), each of which is positioned between one of the return springs (13, 14) and the other end of the driving spring (11).

20 Claims, 4 Drawing Sheets

PUNCTURING DEVICE

This application is the U.S. National Stage of PCT/PL03/00132, filed Dec. 1, 2003, which claims priority from P.361490, filed Jul. 29, 2003.

BACKGROUND OF THE INVENTION

1. Field of the Invention

This invention relates to the puncturing device designed particularly for puncturing patient's skin in order to collect a blood sample for diagnostic purposes.

2. Description of the Related Art

The U.S. Pat. No. 5,356,420 discloses a puncturing device comprising a sleeve and a push element positioned at the first end of the sleeve. The other end of the sleeve ends with a bottom with an opening therein. Inside the sleeve a piston is slidably mounted, terminating with a push rod at the end closer to the push button, and with a puncturing tip at the end closer to the bottom opening. Inside the sleeve between the push element face and the piston, a drive spring is located, and between the piston and the sleeve bottom a return spring is placed. The piston comprises wings located on its outer perimeter which rest on an internal projection of the sleeve.

Further, the U.S. Pat. No. 5,439,473 discloses a lancet designed for puncturing patient's skin for the sake of collecting small blood samples. The lancet has elongated housing, wherein a movable member is disposed sliding along the housing axis, while the housing has a top opening for the lancet push button, and a bottom opening for the piercing blade. The movable member consists of a flat spring, one end of which is linked to the push button. The push button has two upper arms perpendicular to its surface, and those arms have hooked ends disposed in oblong openings of the housing side walls. The other end of the movable member flat spring is joined with a holder wherein the piercing blade is fixed. The holder lower portion has two lower arms parallel to the upper arms. The lower arms have moreover upwardly directed, triangle shaped tips, which rest upon the lower edges of the oblong openings of the housing walls. All parts of the movable member are made of plastics.

When the patient's skin is being punctured, the lancet press button is pressed, by what the flat spring of the movable member is tensed, and hooked ends of the upper arms press against the tips of the lower arms of the movable member. Next the release of the lower arms occurs, the flat spring rebounds, and the patient's skin is punctured by the piercing blade which passes through the housing bottom opening. After puncturing the flat spring assumes free position, and the piercing blade retracts inside the lancet housing.

Further, the U.S. Pat. No. 5,755,733 discloses a lancet device consisting of a lancet assembly and a holder linked to the lancet assembly, wherein the lancet assembly has a lancet with piercing portion, and an ejector which pushes the lancet out. In the known lancet device the lancet piercing portion is covered with plastic material.

SUMMARY OF THE INVENTION

According to the present invention, the puncturing device comprises a housing wherein the push button and the puncturing needle is disposed, wherein the push button has arms to guide the push button inside the housing, and a driving spring, one end of which is linked to the push button, and the other end drives the puncturing needle, and the puncturing needle has breakable wings which rest against the breaking edge of the housing, and it comprises at least one return spring connected to the push button arms, while the puncturing needle has at least one side jut disposed inside the device between the return spring and the other end of the driving spring.

Preferably it has two return springs, each of which is connected to one arm of the push button, and two side juts, each of which is disposed inside the device between one of the return springs and the other end of the driving spring.

Preferably the return springs are connected approximately perpendicularly to the lower portions of the push button arms.

Preferably the first end of the driving spring is connected to the push button face.

Preferably the other end of the driving spring ends with a pusher for the puncturing needle.

Preferably the driving spring is S-letter shaped.

Preferably the return springs are flat springs.

An advantage of the solution according to the present invention is a fact that it facilitates puncturing the patient's skin in a safe and cost-efficient manner.

BRIEF DESCRIPTION OF THE DRAWINGS

The accompanying drawings, which are incorporated in, and form a part of the specification, illustrate the embodiment of the present invention and, together with the description, serve to explain the principles of the invention. In the drawings.

DETAILED DESCRIPTION OF THE INVENTION

Reference will now be made in detail to the preferred embodiment of the invention, the example of which is illustrated in the accompanying drawings.

Figure 1:
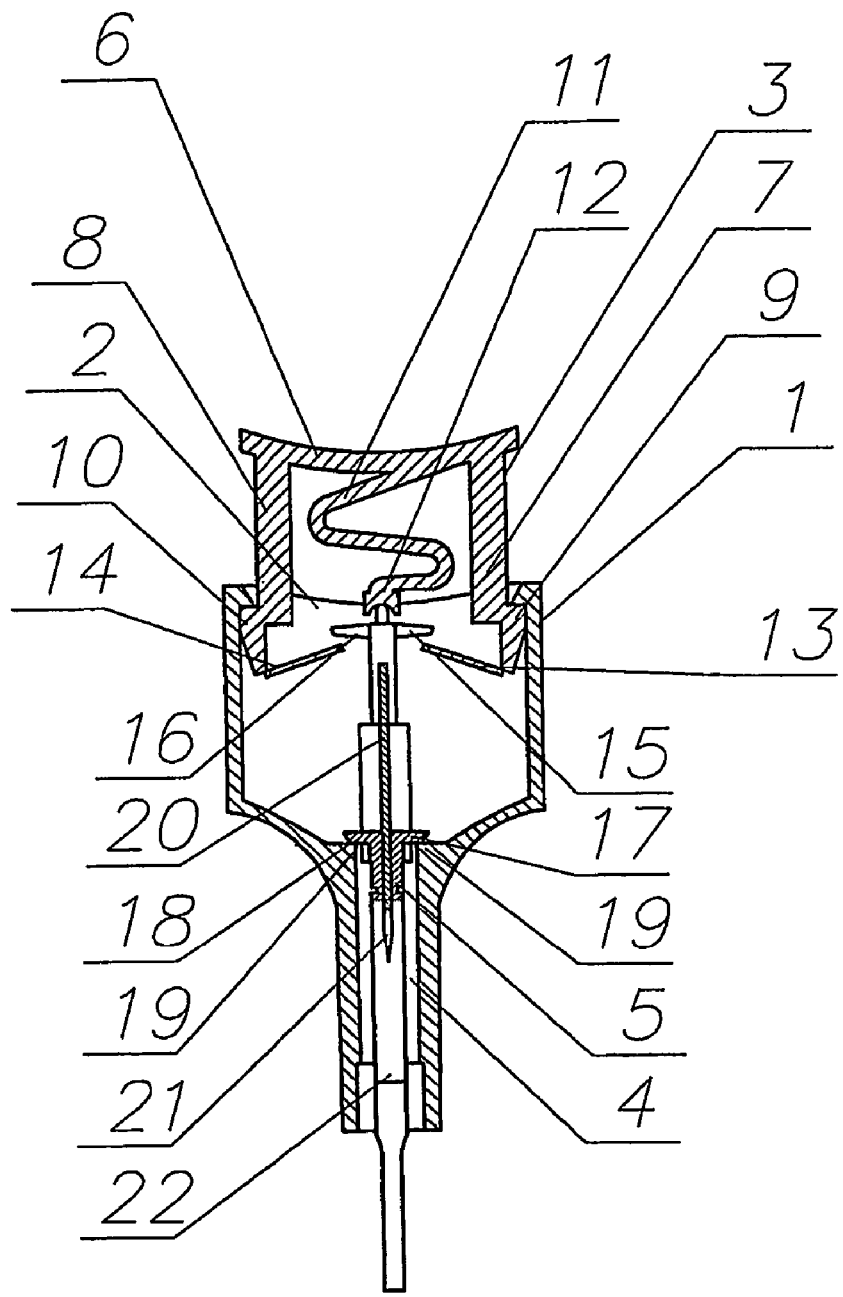
FIG. 1 shows the longitudinal section of the puncturing device according to the invention before use.

The puncturing device depicted in the FIG. 1 is built of a housing (1), where in the top opening (2) of the housing a push button (3) is positioned, while in the lower, elongated opening (4) of the housing (1) is in turn disposed the puncturing needle (5). The push button (3) is made of plastic, and consists of the push button face (6) and parallel to the housing (1) axis and expanding from the opposite ends of the push button face (6) arms (7, 8) to guide the push button (3) in the housing (1). Each of the arms (7, 8) has also a detent (9, 10) to fix the push button (3) in the housing (1). Moreover the push button (3) has a driving spring (11) shaped like the letter "S", which is linked on one side to the push button face (6), and on the other end tipped with the pusher (12) for the puncturing needle (5), and has two flat return springs (13, 14), each of which is mounted approximately perpendicular to lower portions of the arms (7, 8) of the push button (3). The puncturing needle (5), which is disposed in the lower, oblong opening (4) of the housing (1), has in its upper portion two side juts (15, 16), which are disposed in the device according to the invention between the pusher (12) of the driving spring (11) of the push button (3), and the return springs (13, 14), and in its lower portion breakable wings (17, 18), which rest against the upper edge of the lower, elongated opening (4), which is the breaking edge (19) for the wings (17, 18). Inside the puncturing needle (5) a lancet (20) is disposed, while the puncturing portion (21) of the lancet (20) has a shield (22) of plastic.

Figure 2:
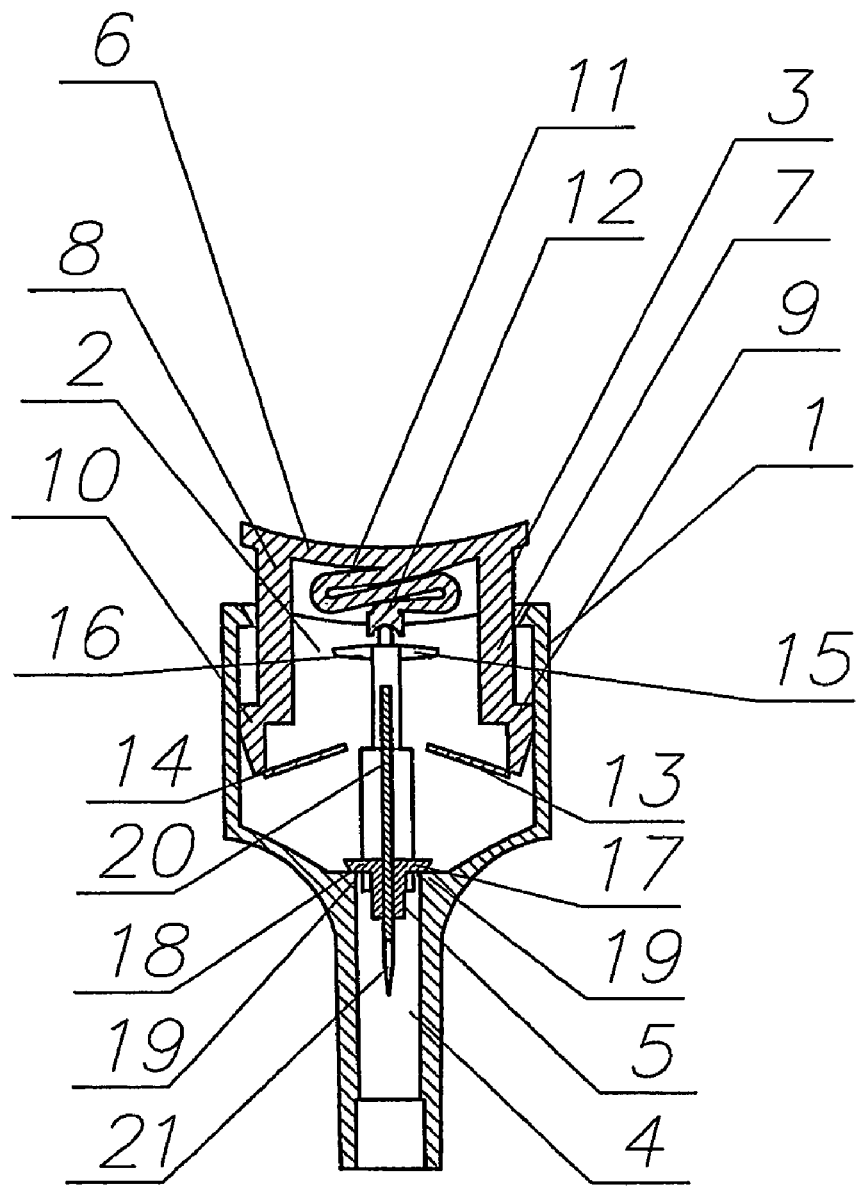
FIG. 2 shows the device from the FIG. 1 before breaking the wings.
Figure 3:
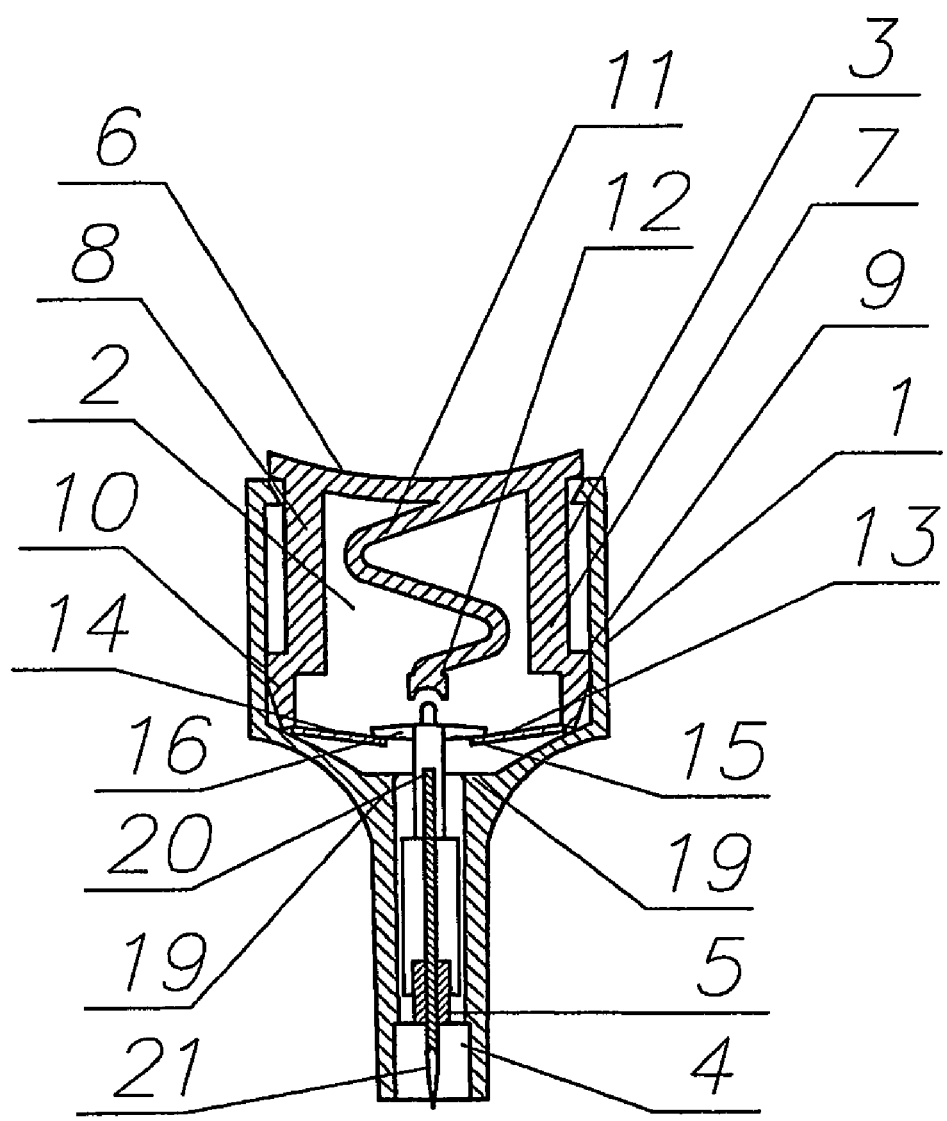
FIG. 3 shows the device from the FIG. 1 after breaking the wings.
Figure 4:
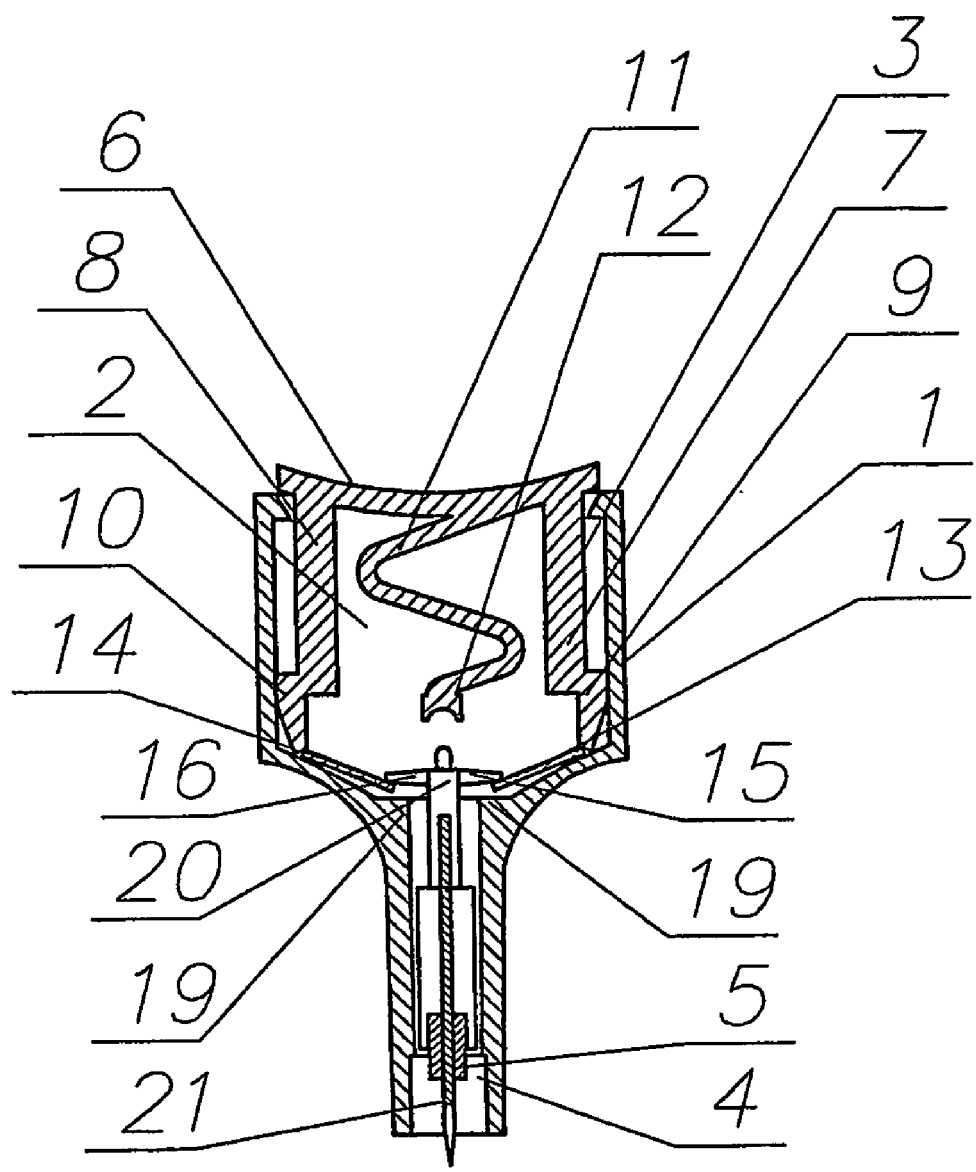
FIG. 4 shows the device from the FIG. 1 during puncturing the patient's skin, whereas the same elements of the puncturing devices depicted on the drawing have the same designations.

The operation of the device according to the invention is as follows:

The position of the device elements before use is shown in the FIG. 1, where the push button (3) is in the upper position, and the breakable wings (17, 18) rest against the breaking edge (19). After detachment of the shield (22) of the piercing portion (21) of the lancet (20), the push button face (6) is pressed, causing compressing the driving spring (11), as it is depicted in the FIG. 2, to the moment when the driving spring (11) is maximally compressed, and breaking off the wings (17, 18) occurs. Then the driving spring (11) expands, in result of which the puncturing needle (5) with the lancet (20) displaces in the lower opening (4) of the housing (1), while the side juts (15, 16) of the puncturing needle (5) press the return springs (13, 14), as it is shown in the FIG. 3. Next the puncturing portion (21) of the lancet (20), protruding outside the lower opening (4) of the housing (1) punctures the patient's skin, while the side juts (15, 16) of the puncturing needle (5) cause maximum deflection of the return springs (13, 14), as it is shown in the FIG. 4. After puncturing the skin, the return springs (13, 14) pull, with the help of the side juts (15, 16), the puncturing needle (5) inside the lower opening (4) of the housing (1), while the driving spring (11) and the return springs (13, 14) are then in free state, as it is shown in the FIG. 3.

Subsequent re-use of the device is not possible because the wings (17, 18) of the puncturing needle (5) are already broken off.

I claim:

1. A puncturing device comprising:
    a housing, wherein the housing defines a breaking edge;
    a puncturing needle disposed in the housing, wherein the puncturing needle has breakable wings that rest against the breaking edge of the housing, and at least one side jut;
    a push button disposed in the housing, wherein the push button has arms to guide the push button inside the housing;
    at least one return spring, wherein each of the at least one return spring is directly connected to an arm of the arms, and wherein the at least one return spring has a contact portion that contacts the at least one side jut; and
    a driving spring having a first end and a second end, wherein the first end is linked to the push button and the second end drives the puncturing needle in a driving direction parallel to a longitudinal axis defined by the puncturing needle,
    wherein the entirety of the at least one side jut of the puncturing needle is disposed inside the housing longitudinally between the contact portion of the at least one return spring and the second end of the driving spring before, during, and after use of the puncturing device, such that the contact portion of the at least one return spring, the entirety of the at least one side jut, and the driving spring are disposed in non-overlapping series along the longitudinal axis before, during, and after use of the puncturing device, and
    wherein the at least one return spring acts against the at least one side jut in a direction generally opposite to the driving direction.

2. The puncturing device according to the claim 1, wherein the at least one return spring comprises two return springs, each of which is connected to an arm of the arms, and wherein the at least one side jut comprises two side juts, each of which is positioned inside the device longitudinally between the contact portions of the two return springs and the second end of the driving spring before, during, and after use of the puncturing device, such that the two return springs, the two side juts, and the driving spring are disposed in series along the longitudinal axis before, during, and after use of the puncturing device.

3. The puncturing device according to the claim 2, wherein the two side juts each comprise an elongate member that extends perpendicularly to the longitudinal axis and defines a first jut surface facing the driving spring, a second jut surface opposite to the first surface, and a distal edge between the first jut surface and the second jut surface and facing away from the longitudinal axis,
    wherein the two return springs are connected approximately perpendicularly to the lower portions of the arms of the push button,
    wherein each of the two return springs comprises a flat member defining a plane,
    wherein the flat member extends toward the puncturing needle such that the plane of the flat member is generally perpendicular to and generally radial to the longitudinal axis,
    wherein the flat member defines a first return spring surface facing the second jut surface and a second return spring surface opposite to the first return spring surface,
    wherein the first return spring surface and the second jut surface remain facing each other before, during, and after use of the puncturing device, and
    wherein the first return spring surface contacts the second jut surface to move the puncturing needle in a direction opposite to the driving direction and parallel to the longitudinal axis.

4. The puncturing device according to the claim 1, wherein the driving spring is integrally formed with the push button and extends from an inside face of the push button.

5. The puncturing device according to the claim 1, wherein the second end of the driving spring comprises a pusher that pushes the puncturing needle.

6. The puncturing device according to claim 5, wherein the puncturing needle and the pusher are separate structures, wherein the pusher contacts the puncturing needle during operation of the puncturing device, and discontinues contact with the puncturing needle after use such that the pusher becomes discontinuous with the puncturing needle after use.

7. The puncturing device according to claim 5, wherein the pusher has a cup-shaped end and wherein the puncturing needle has a projection that fits within the cup-shaped end of the pusher.

8. The puncturing device according to the claim 1, wherein the driving spring is shaped like the letter "S".

9. The puncturing device according to the claim 1, wherein the at least one return spring is a flat spring.

10. The puncturing device according to claim 1, wherein a first force applied to the push button compresses the driving spring between the push button and the puncturing needle and presses the breakable wings against the breaking edge until the breakable wings break,
    wherein, upon breaking the breakable wings, the driving spring drives the puncturing needle such that a lancet of the puncturing needle extends outside the housing and the at least one side jut contacts the at least one return spring, and
    wherein, after the lancet extends outside the housing, the at least one return spring applies a second force to the at least one side jut in a direction generally parallel to the longitudinal axis and opposite to the first force to pull the lancet of the puncturing needle inside the housing.

11. The puncturing device according to claim 10, wherein after pulling the lancet of the puncturing needle inside the housing, the at least one return spring and the driving spring are in a free state.

12. The puncturing device according to claim 1, wherein the arms are integral to the push button before, during, and after use of the puncturing device.

13. The puncturing device according to claim 1, wherein each of the arms of the push button defines a detent contained within the housing, wherein the detent contacts an interior portion of the housing to prevent removal of the push button from the housing, and wherein the each of the at least one return spring is directly connected to the detent of the arm.

14. The puncturing device according to claim 1, wherein the puncturing needle has a first end driven by the driving spring and a second end comprising a puncturing portion, wherein the at least one side jut is disposed on the puncturing needle proximate to the first end of the puncturing needle and proximate to the second end of the driving spring.

15. The puncturing device according to claim 1, wherein the puncturing needle has a first end driven by the driving spring and a second end comprising a puncturing portion, wherein the at least one side jut is disposed on the puncturing needle closer to the first end of the puncturing needle than the second end of the puncturing needle, and wherein the breakable wings are disposed on the puncturing needle closer to the second end of the puncturing needle than the first end of the puncturing needle.

16. The puncturing device according to claim 1, wherein the at least one return spring acts against the at least one side jut in a direction generally parallel to the longitudinal axis and opposite to the driving direction after a lancet of the puncturing needle extends outside the housing, to pull the lancet in a direction opposite the driving direction along the longitudinal axis and back inside the housing.

17. The puncturing device of claim 1, wherein the push button, the arms, the at least one return spring, and the driving spring are integrally formed as a single continuous part.

18. A puncturing device comprising:
a housing, wherein the housing defines a breaking edge;
a puncturing needle disposed in the housing, wherein the puncturing needle has an upper pushing end and a lower puncturing end, wherein the puncturing needle defines a longitudinal axis along which the puncturing needle travels, and wherein the puncturing needle comprises:
an elongated body extending longitudinally;
a breakable wing protruding from the body in a direction perpendicular to the longitudinal axis, wherein the breakable wing rests against the breaking edge of the housing before use of the puncturing device, and
a jut member protruding from the body in the direction perpendicular to the longitudinal axis,
wherein the breakable wing is disposed closer to the puncturing end than the jut member, and
wherein the jut member defines a lower contact face facing the puncturing end of the needle and an upper face opposite to the lower contact face;
a push button disposed in the housing, the push button comprising:
a button face extending in a direction perpendicular to the longitudinal axis and disposed over the upper pushing end of the puncturing needle,
an arm extending from the button face in a direction toward the lower puncturing end of the puncturing needle and parallel to the longitudinal axis, wherein the arm guides movement of the push button within the housing, and
a return spring directly connected to the arm, the return spring defining an upper contact surface that contacts the lower contact face of the jut member; and
a driving spring disposed between the button face of the push button and the pushing end of the puncturing needle, wherein the driving spring is discontinuous with the puncturing needle, and
wherein before, during, and after use of the puncturing device, the lower contact surface of the jut member faces the upper contact surface of the return spring.

19. The puncturing device of claim 18, wherein during use of the puncturing device, the driving spring and the puncturing needle separate from each other such that a gap exists between the driving spring and the puncturing needle.

20. The puncturing device of claim 18, wherein the push button face, the arm, the return spring, and the driving spring are integrally formed as a single continuous part.

* * * * *